June 23, 1953 M. L. WHISLER Plant Pat. 1,200
ROSE PLANT
Filed Sept. 26, 1951
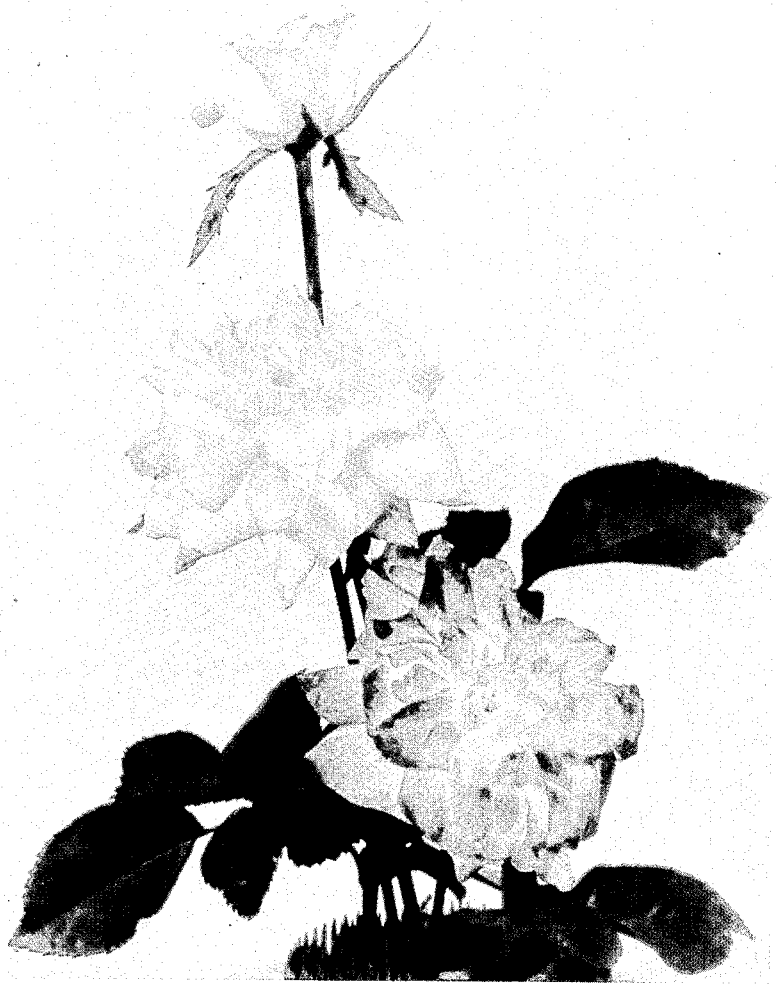
Inventor.
M. L. Whisler
By: Robert Cobb
Attorneys.

Patented June 23, 1953

Plant Pat. 1,200

UNITED STATES PATENT OFFICE 1,200

ROSE PLANT

Milton L. Whisler, Van Nuys, Calif., assignor to Germain's, Inc., Van Nuys, Calif., a corporation of California Application September 26, 1951, Serial No. 248,297

1 Claim. (Cl. 47—61)

The present invention relates to a new and distinct variety of rose plant of the hybrid polyantha class, originated by me by crossing the variety "Sunshine" (unpatented) × the variety "Herrenhausen" (unpatented).

As the result of this cross, I have produced a new variety which is substantially different from its parents as well as from other varieties of this class, but which resembles the parent "Herrenhausen" more than any other variety, yet is distinctly different from this parent by being more free-flowering, more dwarf in its habit of growth, and having a wider range of color in its flowers as the individual flowers age.

Besides these primary features of novelty and distinctiveness above referred to, my new variety is outstanding because of the great abundance of blooms produced thereby, and also because of the unusual coloring characteristics of the blooms as illustrated in the accompanying illustration and as hereinafter more particularly described.

Asexual reproduction of this new variety by cuttings, grafting and budding at Van Nuys, California, shows that the foregoing characteristics come true to form and are established and transmitted through succeeding propagations.

The accompanying drawing shows specimens of the flowers and foliage of the new variety in different stages of development.

The following is a detailed description of the new variety, with color terminology in accordance with the Horticultural Color Chart of the British Color Council, except where general color terms of ordinary dictionary significance are obvious:

Type: Half hardy; dwarf; bush; seedling; for garden decoration.

Class: Hybrid polyantha.

Breeding: Seedling.

*Seed parent.*—"Sunshine."

*Pollen parent.*—"Herrenhausen."

Propagation: Holds its distinguishing characteristics through succeeding propagations by cuttings, grafting and budding.

*Flower*

Locality where grown and observed: Van Nuys, California.

Flowers borne: Singly to stem; in irregular, flat cluster; on strong, medium length stems.

Quantity of bloom: Abundant; outdoors.

Continuity: Intermittent.

Fragrance: Slight; sweetbriar.

Bud:

*Peduncle.*—Medium length; stiff; reddish purple; numerous brown hairs.

*Before calyx breaks.*—Size—small. Form—short; ovoid; with foliaceous appendages on the surface of the bud; with stout foliaceous parts extending beyond the tip of the bud equal to ½ or more of its length. Color—green, blotched purple and brown.

*As calyx breaks.*—Color—Aureolin, Plate 3/1, shaded Geranium Lake, Plate 20/3, where sunlight strikes petals not covered by sepals.

*As first petal opens.*—Size—small. Form—short; flat. Color: outside — Aureolin, Plate 3/2, shaded Geranium Lake, Plate 20/2 to 20/3, where petals are not covered by sepals; inside—Aureolin, Plate 3/1.

*Opening.*—Opens up well.

Bloom:

*Size, when fully open.*—Small; 2½ inches to 3 inches.

*Petalage.*—Very double; from 50 to 60 petals; arranged irregularly.

*Form.*—Cupped at first; becoming open; petals being at first loosely cupped; becoming later, at maturity, flat-cupped.

Petals: Thick; soft; with inside shiny and outside satiny.

*Shape.* — Outside—obovate; intermediate—oval.

This description of a newly opened flower was made from a rose grown outdoors in the month of August, at Van Nuys, California.

*Color.* — Outside petal. outside surface—Aureolin, Plate 3/2; inside surface—Aureolin, Plate 3/1, shaded Geranium Lake, Plate 20/2, where sunlight strikes petals. Intermediate petal: outside surface—Aureolin, Plate 3/1; inside surface—Aureolin, Plate 3/1, shaded Geranium Lake, Plate 20/2, where sunlight strikes petals. Inner petal: outside surface—Aureolin, Plate 3/1; inside surface—Aureolin, Plate 3/1, shaded Geranium Lake, Plate 20/2, where sunlight strikes petals.

This description was made from a rose that was open for three days outdoors in the month of August, at Van Nuys, California.

*Color.*—Outside petal: outside surface—Aureolin, Plate 3/2; inside surface—Aureolin, Plate 3/3, shaded Geranium Lake, Plate 20/2. Inside petal: outside surface—Aureolin, Plate 3/2; inside surface—Aureolin, Plate 3/3, shaded Geranium Lake, Plate 20/2.

*General color effect.*—Newly opened flower—Aureolin, Plate 3/1, shaded Geranium Lake, Plate 20/2 to 20/3. Three days open—Geranium Lake, Plate 20/2 to Turkey Red, Plate 721/2.

*Behavior.*—Persist; fading brown; shading to shades of red takes place only on areas exposed to sunlight.

*Flower longevity.*—On bush in garden—5 days in August. Cut roses, grown outdoors, kept at living room temperature—4 days in August.

*Reproductive organs*

Stamens: Very few, arranged irregularly; mixed with petaloids.

Filaments: Short; most with anthers. Color—some Lemon Yellow, Plate 4/3, some Nasturtium Red, Plate 14/3.

Anthers: Small; open at various times. Color—Chrome Yellow, Plate 605/1.

Pollen: Sparse. Color—gold.

Pistils: Few.

Styles: Uneven; medium length; thin; loosely bunched.

Stigma: Color—yellow.

Ovaries: Some protruding from calyx.

Hips: Short; globular; moderately smooth; walls thin, dry. Color—brown-reddish.

Sepals: Falling soon; long; recurved. Color—grey-green.

*Plant*

Foliage:

*Leaves.*—Compound of five leaflets; normal abundance; medium size; heavy; leathery.

*Leaflet.*—Shape—oval, with apex acute. Base—round. Margin—doubly serrate.

*Color.*—Mature: upper surface—dark green; under surface—normal green. Young: upper surface—green-bronze; under surface—bronze-red.

*Rachis.*—Medium weight. Upper side—grooved; hairy. Under side—sparsely prickly.

*Stipules.*—Medium length; wide; with medium length points turning out at an angle of more than 45°.

*Disease.*—Resistant to mildew, as determined by comparison with other varieties grown under comparable cultural conditions at Van Nuys, California.

Growth:

*Habit.*—Dwarf; bushy, much branched.

*Growth.*—Moderately vigorous.

*Canes.*—Medium size.

*Main stems.* — Color — dull grey - green. Thorns—few; long; straight; with long, narrow base. Prickles—none. Hairs—none.

*Branches.* — Color — dull grey - green. Thorns—few; long; straight; with long, narrow base. Prickles—none. Hairs—several; color—brown.

*New shoots.*—Color—dull red. Thorns—several; straight; with long, narrow base. Prickles—none. Hairs—none.

I claim:

A new and distinct variety of rose plant of the hybrid polyantha class, substantially as herein shown and described, characterized as to novelty by its dwarf habit of growth, by its free-flowing habit and abundance of flowers borne thereby, by the distinctive coloring of the flowers, and by the changing colors thereof through a relatively wide range as the flowers age.

MILTON L. WHISLER.

No references cited.